United States Patent [19]
Freytag et al.

[11] 3,957,047
[45] May 18, 1976

[54] RESPIRATION-TIME CONTROL DEVICE IN RESPIRATORS FOR INFANTS

[75] Inventors: Klaus Freytag, Bad Schwartau; Detlef Warnow, Lubeck, both of Germany

[73] Assignee: Drägerwerk Aktiengesellschaft, Germany

[22] Filed: Feb. 6, 1975

[21] Appl. No.: 547,501

[30] Foreign Application Priority Data
Feb. 8, 1974 Germany............................ 2405955

[52] U.S. Cl............................. 128/145.8; 128/142.3
[51] Int. Cl.²........................................ A61M 16/00
[58] Field of Search........... 128/145.8, 145.6, 145.5, 128/142, 142.3

[56] References Cited
UNITED STATES PATENTS

| | | | |
|---|---|---|---|
| 3,662,751 | 5/1972 | Barkalow et al................. | 128/145.8 |
| 3,739,775 | 6/1973 | Helm et al....................... | 128/145.8 |
| 3,754,550 | 8/1973 | Kipling............................ | 128/145.8 |
| 3,889,669 | 6/1975 | Weigl.............................. | 128/145.8 |

*Primary Examiner*—Robert W. Michell
*Assistant Examiner*—Henry J. Recla
*Attorney, Agent, or Firm*—McGlew and Tuttle

[57] ABSTRACT

The respirator includes a breathing gas supply line connected, through a distribution piece, to a mouthpiece, and also connected to a breathing gas discharge line having interposed therein a control valve controlling discharge of expirated breathing gas, the control valve being switched between opened and closed positions with the aid of a pressure-sensitive control means. An actual value pointer is connected to and operable by the pressure-sensitive control means, and two air barriers are positioned in the range of movement of the pointer for interruption by the pointer. One air barrier constitutes a frequency air barrier which closes the control valve by a pressure signal responsive to interruption of the frequency air barrier by the pointer. The other air barrier constitutes an inspiration-time air barrier which effects opening of the control valve by a pressure signal responsive to interruption of the inspiration-time air barrier by the pointer. The two air barriers are displaceable in the range of movement of the actual-value pointer to provide for simple adjustment of the respiration frequency, the inspiration and expiration time, and the ratio of the inspiration time to the expiration time. The control components are pneumo-logical components, and the frequency air barrier is connected to a charging accumulator controlled by a choke and a capacitance, the charging accumulator being also connected to the pressure-sensitive control means.

6 Claims, 1 Drawing Figure

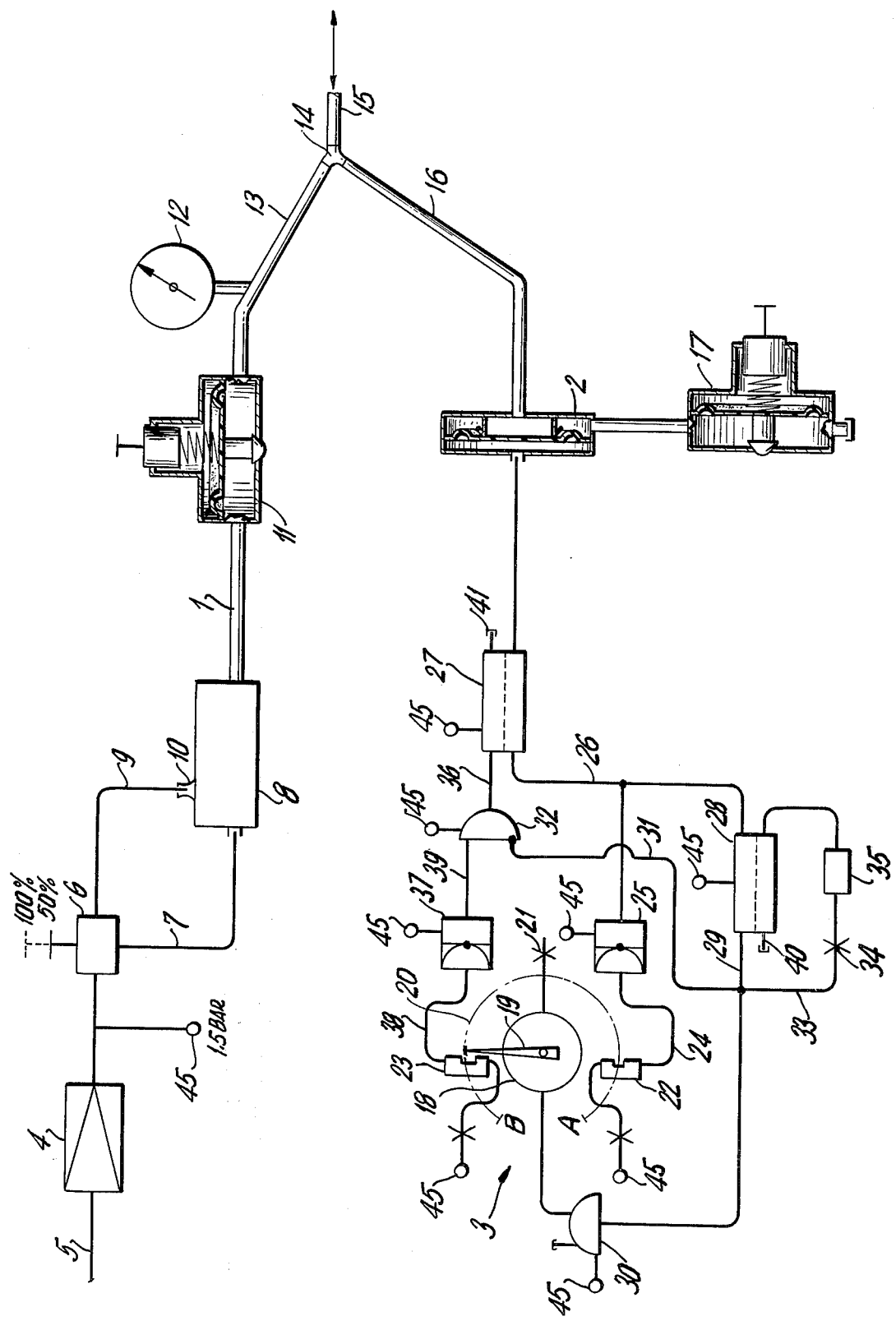

RESPIRATION-TIME CONTROL DEVICE IN RESPIRATORS FOR INFANTS

FIELD AND BACKGROUND OF THE INVENTION

This invention relates to a respiration-time control device in a respirator for infants in which the control valve is switched with the aid of a pressure-sensitive control means.

Respirators for infants have to comply with particular requirements. Thus, a relatively small respiration volume must be supplied at a frequency as high as possible and under exactly controlled conditions, and a high dead space ventilation must be avoided. The time control device for controlling the operations of the respiration cycle has to work with a corresponding accuracy.

In a known respirator for infants, breathing air is supplied to the patient, during the inspiration phase, under the control of a switch valve and, during the expiration phase, the air is evacuated. The respiration frequency is adjustable and the ratio of inspiration time to expiration time can be chosen. For inspiration, the switch valve opens the supply line conducting breathing gas to the patient and, for expiration, this line is shut off and the expiration line is opened instead. The supply line comprises a relief valve preventing an excessive peak pressure. The time control of the switch valve is effected by means of an electronic oscillator adapted for the adjustment both of the frequency and the ratio of the inspiration time to the expiration time. The time control device works electronically. This is disadvantageous since, due to the composition of two sorts of energy, namely electricity and pressure gas, the apparatus is complicated and not simple in use (Loosco prospectus No. 681 008).

Another known respirator for infants permits spontaneous respiration and time-controlled respiration in a purely pneumatic way. In both cases, the breathing gas flows continuously in the supply line in the direction of the patient and then, through the expiration line and the expiration valve, to the outsie. Close to the patient, the two lines are united in a connection piece wherefrom only one conduit leads to the user. During the spontaneous respiration, the patient takes the breathing gas from the flowing stream and exhales it again into the flowing stream. The patient determines the respiration phases and respiration frequencies. The counterpressure in the breathing gas stream is small and is overcome.

During time-controlled respiration, the sequence of the respiration phases is determined by the opening and closing of the expiration valve. With the expiration valve closed, the full breathing gas stream flows to the patient. The expiration phase is started by the opening of the expiration valve. Then the breathing gas stream, in which the exhalation stream is admixed in the connection piece, flows past the patient to the expiration valve. The time control device, for assuring actuation of the expiration valve at the right instants, comprises a plurality of systems of pneumatic component parts. This very circumstance is the drawback of the respirator. It is difficult to exactly control the different systems which, in addition, are interdependent in their operation. Only an accurate adjustment of all of the elements and their continuous checking can ensure the desired values of the respiration frequency and the ratio of the inspiration time to the expiration time. The adjustment and securing of the control during the respiration is made particularly difficult in the treatment of infants by the required small respiration volume at a high respiration frequency (Babybird-Ventilator-Bird-Corporation 1972, Form 5900.2).

In another proposed respirator, the respiration phases are controlled, both in time and spontaneously, by the patient. By pressure signals furnished by a control device, a gas-pressure-controlled valve is opened and closed. In the inspiration phase, the breathing gas flows through the opened valve to the patient. Pressure controlled by the patient himself or in accordance with the adjusted time, the valve closes and terminates the inspiration phase. The expiration air flows to the outside along a separate path. The control device, both for the time-controlled respiration and the spontaneous respiration, is a pressure-controlled control means comprising an actual-value pointer whose range of deflection is limited by a displaceable air barrier at each side, where the pointer, upon entering, interrupts a continuously flowing control stream and thereby furnishes a pressure signal. However, this respirator cannot be used for infants without further provisions.

SUMMARY OF THE INVENTION

The present invention is directed to a time control device in respirators for infants, coping in a simple and reliable manner with all of the requirements for a respiration with small respiration volumes, at a high respiration frequency and with a small dead-space ventilation. It permits an easy adjustment and a simple maintenance.

In accordance with the invention, the control means is connected to an actual-value pointer moving in the range of two air barriers of which one, as a frequency air barrier, closes the control valve by a pressure signal while the other, as an inspiration-time air barrier, opens the control valve. The presssure signals are released by the actual-value pointer in the frequency air barrier or in the inspiration-time air barrier. With the closing of the control valve, the expiration phase is terminated and, with subsequent inspiration phase, a new respiration cycle is started. The inspiration phase ends with the opening of the control valve. The frequency air barrier and the inspiration-time air barrier are displaceable within the range of deflection of the actual-value pointer of the control device. The frequency air barrier is connected to a charging accumulator which is controlled by a choke and a capacitance, and the charging accumulator is connected to the control means.

The advantages obtained by the invention are to be seen particularly in the fact that the control of the respiration phases and of the respiration frequency is effected merely by two simple changes in the time control system, namely by the displacement of the two air barriers, ie., the frequency air barrier and the inspiration-time air barrier, within the range of deflection of the actual-value pointer. The adjustment of the ratio of the inspiration time to the expiration time ratio is effected in the same simple manner. The other time-determining factors in the system are constants. One of them is a choke in the pressure-sensitive control means, through which the gas filling flows off and the other is a choke on the charging accumulator, followed by a capacitance. The air barriers can be adjusted very accurately so that the switch times of the control valve can be controlled very well. The condition of maintaining a small respiration volume for infants is met, and no difficulties arise as to the high respiration frequencies either. The position of the frequency air barrier along determines the respiration frequency.

A very advantageous feature is the use, in the respiration-time control device, of pneumo-logical component parts, because of their well known high reliability in operation and long service life without maintenance expenses.

An object of the invention is to provide an improved respiration-time control device in respirators for infants.

Another object of the invention is to provide such a respiration-time control device which is capable of easy adjustment and simple maintenance.

A further object of the invention is to provide such a respiration-time control device including pneumo-logical component parts having high reliability in operation and a long service life without maintenance expenses.

These and other objects of the invention will be apparent from the following description of a typical embodiment of the invention as shown in the accompanying drawing.

BRIEF DESCRIPTION OF THE DRAWING

In the Drawing:

The single FIGURE of the drawing is a diagrammatic representation of one embodiment of a respiration-time control device in a respirator for infants.

DESCRIPTION OF THE PREFERRED EMBODIMENT

The respiration-time control device is a part of a respirator for infants. The respirator comprises a part 1, conducting the breathing gas and ending with the control valve 2, and the respiration-time control device 3. The part 1 conducting the breathing gas comprises a pressure reducer 4 in which the high-pressure breathing gas supplied at 5 is reduced to a pressure of approximately 1.5 bar. In a bypass valve 6, the breathing-gas stream is branched into a partial stream 7, flowing directly into the antechamber 8, and a partial stream 9, flowing into the antechamber 8 through the injector 10. Antechamber 8 is followed by an inspiration-pressure valve 11 in which the chosen respiration pressure is adjusted and controlled. A respiration-pressure gauge 12 indicates the pressure in the breathing-gas supply line 13. Inspiration-pressure valve 11 ensures that the patient is not charged with a pressure peak in each inspiration phase. The pressure in the breathing gas reaches only the valve controlled in inspiration-pressure valve 11 and is then supplied at a relatively constant level.

Gas supply line 13 branches, in a distribution piece 14, into a branch 15 leading directly to the patient and a branch 16 leading to control valve 2. With control valve 2 closed, all breathing gas flows to the patient. With control valve 2 opened, the breathing gas flows through branch 16 directly to control valve 2. The air exhaled by the patient mixes, in distribution piece 14, with the stream of breathing gas and flows out along therewith, through control valve 2 and the following expiration-pressure valve 17. Expiration-pressure valve 17 makes it possible for the patient to exhale against a pressure, which may be desirable for medical reasons.

By opening and closing control valve 2, the respiration phases, the respiration frequency and the ratio of the inspiration time are controlled. This is effected by means of respiration-time control device 3. The device comprises the pressure-sensitive control means 18 equipped with the actual-value pointer 19. Actual-value pointer 19 has a range of deflection 20 limited at A and B. After being filled with pressure gas, control means 18 is evacuated through choke 21. During the filling, actual-value pointer 19 is turned to B and, during the evacuation, it travels toward A.

The frequency air barrier 22 and the inspiration-time air barrier 23 are mounted for displacement within the range of deflection 20. As actual-value pointer 19 passes through either air barrier 22, 23, a respective continuous pneumatic signal thereof is interrupted and, thereby, a respective pressure signal is released. Through line 24, the pressure signal coming from frequency air barrier 22 switches a NINO element 25, which is connected as a negation, to pressure at the outlet. Thereupon, through line 26, the pressure switches accumulator 27 to pressure by which control valve 2 is closed. Consequently, the patient receives breathing gas.

At the same time, the pressure in line 26 switches the charging accumulator 28 to output. Through line 29 and identity element 30, control means 18 is filled up. In consequence, actual-value pointer 19 moves into the end position B of the range of deflection 20. A NAND element 32 is connected to line 29 through line 31, and charging accumulator 28, with an interconnected choke 34 and capacitance 35, is connected to line 29 through line 33. If, during the passage of actual-value pointer 19 through inspiration-time air barrier 23 toward B, a NINO element 37, connected to negation, receives a pressure signal through line 38 and applies pressure, through line 39, to NAND element 32, the pressure applied to NAND element 32 through line 31 prevents a switching of the pressure to line 36 and accumulator 27.

In this phase, charging accumulator 28 is filled through choke 34 and capacitance 35, and channels to outlet 40. Thereby, line 29 becomes pressureless and supply of pressure gas to control means 18 is stopped. At this moment, due to an appropriate dimensioning of choke 34 and capacitance 35, actual-value pointer 19 certainly has reached its end position B and dwells. Switching of accumulator 28 makes line 31 and, therefore, NAND element 32, also pressureless. As the filling of control means 18 is terminated, evacuation through choke 21 is instantly started, and actual-value pointer 19 moves back toward A. This time, at the passage through inspiration-time air barrier 23, the released pressure signal acts through NINO element 37 and NAND element 32, which is no longer under pressure from line 31, and switches the pressure to outlet 41 of accumulator 27. Thereby, control valve 2 becomes pressureless and opens. The respiration gas can flow off through valve 17, and the expiration phase begins for the patient. Control means 18 is further continuously evacuated and actual-value pointer 19 moves necessarily along. As it enters the frequency air barrier 22, a pressure signal is released again, closing control valve 2. The inspiration phase recommences.

The respiration-time control device makes it possible to adjust
  a. the respiration frequency,
  b. the inspiration and expiration time, and
  c. the inspiration to expiration time ratio.

The adjustment is effected by displacing air barriers 22, 23 within the range of deflection of actual-value pointer 19. First, the respiration frequency is to be adjusted.

To (a) The respiration frequency is determined by the constants of the apparatus and the inspiration and expiration time. It can be adjusted by positional adjustment of frequency air barrier 22.

To (b) The inspiration time is determined by the travel of actual-value pointer 19 from frequency air barrier 22 through B back to inspiration-time air barrier 23. The expiration time results from the mutual spacing of the two air barriers.

To (c) The ratio of inspiration to expiration time is determined by the position of inspiration-time air barrier 23 between B and frequency air barrier 22.

The supply line 45 for all of the pneumatic component parts is branched off downstream of the pressure reducer 4. Only the connections of this line are shown.

While a specific embodiment of the invention has been shown and described in detail to illustrate the application of the principles of the invention, it will be understood that the invention may be embodied otherwise without departing from such principles.

What is claimed is:

1. In a respiration-time control device in respirators for infants of the type including a breathing gas supply line, a branch line connected to the supply line and leading directly to the patient, an expiration line connected to the supply line and the branch line, and a control valve, controlling discharge of expirated breathing gas, in the expiration line and switched between open and closed positions with the aid of said respiration-time control device, the improvement comprising, in combination, a pressure sensitive control means having an actual-value pointer connected to and operable by said pressure-sensitive control means and movable in opposite directions along a path between two limit positions; two air barriers adjustably mounted in spaced relation along said path within the range of movement of said pointer between said limit positions, means for providing respective continuous pneumatic signals through said air barriers, and means on said pointer for interrupting said signals by movement of said pointer across the associated air barrier; one of said air barriers constituting a frequency air barrier; means operatively associating said frequency air barrier with said control valve whereby said control valve is closed by a pressure signal from said frequency air barrier responsive to movement thereacross of said actual-value pointer toward one limit position; the other of said air barriers constituting an inspiration-time air barrier; and means operatively associating said inspiration-time air barrier with said control valve for blocking opening of said control valve by a pressure signal from said inspiration-time air barrier responsive to movement thereacross of said actual-value pointer toward said other limit position and effecting opening of said control valve by a pressure signal from said inspiration-time air barrier responsive to movement thereacross of said actual-value pointer from said other limit position toward said one limit position; whereby the respiration frequency, determined by the constants of the apparatus and the sum of the inspiration and expiration time, is dependent on the position of said frequency air barrier, the inspiration time is determined by the travel of said actual-value pointer from said frequency air barrier to said other limit position and back to said inspiration-time air barrier, the expiration time is determined by the spacing of said two air barriers, and the ratio of the inspiration time to the expiration time is determined by the position of said inspiration-time air barrier between said other limit position and said frequency air barrier.

2. In a respiration-time control device in respirators for infants, the improvement claimed in claim 1, including means mounting said frequency air barrier and said inspiration-time air barrier for respective displacement along said path within the range of deflection of said actual-value pointer between said two limit positions.

3. In a respiration-time control device in respirators for infants, the improvement claimed in claim 1, in which said means operatively associating said frequency air barrier with said control valve includes a charging accumulator controlled by a choke and a capacitance.

4. In a respiration-time control device in respirators for infants, the improvement claimed in claim 3, in which said charging accumulator is connected to said pressure-sensitive control means.

5. In a respiration-time control device in respirators for infants, the improvement claimed in claim 4, including a second accumulator connected to said charging accumulator and to said control valve; and a NAND element having a first input connected to said charging accumulator, a second input receiving the pressure signal from said inspiration-time air barrier, and an output connected to said second accumulator; said NAND element, when pressure is applied at both its inputs, blocking application of pressure to said second accumulator.

6. In a respiration-time control device in respirators for infants, the improvement claimed in claim 1, in which pneumo-logic component parts are used in said respiration-time control device.

* * * * *